(12) United States Patent
Moretti

(10) Patent No.: US 9,284,513 B2
(45) Date of Patent: Mar. 15, 2016

(54) SAGE ODORANT

(71) Applicant: FIRMENICH SA, Geneva (CH)

(72) Inventor: Robert Moretti, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/654,820

(22) PCT Filed: Dec. 2, 2013

(86) PCT No.: PCT/EP2013/075211
§ 371 (c)(1),
(2) Date: Jun. 22, 2015

(87) PCT Pub. No.: WO2014/095321
PCT Pub. Date: Jun. 26, 2014

(65) Prior Publication Data
US 2015/0337235 A1    Nov. 26, 2015

(30) Foreign Application Priority Data
Dec. 20, 2012 (EP) .................................. 12198489

(51) Int. Cl.
*A61K 8/00* (2006.01)
*C11B 9/00* (2006.01)
*A61K 8/34* (2006.01)
*A61Q 5/02* (2006.01)

(52) U.S. Cl.
CPC ............... *C11B 9/0015* (2013.01); *A61K 8/342* (2013.01); *A61Q 5/02* (2013.01); *A61K 2800/5922* (2013.01)

(58) Field of Classification Search
CPC .................................................. C11B 9/0015
USPC .......................................................... 512/25
See application file for complete search history.

(56) References Cited

U.S. PATENT DOCUMENTS

| 2,205,558 A | 6/1940 | Flett |
| 2,838,576 A | 6/1958 | Normant |
| 4,572,795 A | 2/1986 | Kaiser et al. |

FOREIGN PATENT DOCUMENTS

| DE | 1005952 | 4/1957 |
| DE | 2228333 | 6/1980 |
| EP | 86945 | 8/1983 |
| EP | 1213276 | 6/2002 |
| EP | 1411110 | 4/2004 |
| FR | 1136255 | 5/1957 |
| WO | WO2007005025 | 1/2007 |

OTHER PUBLICATIONS

International Search Report and Written Opinion, application PCT/EP2013/075211, mailed Feb. 27, 2014.
Comptes rendus Hebdomadaire des séances de l'Académie des Sciences, 1955, 240, 631-633.
Cuvigny et al., Journal of the Chem. Soc., Chem. Comm. 1984, n° 1, p. 8.
Molander et al., Journal of Organic Chem, 1986, vol. 51, n° 26, 5259-5264.
Trost et al., J. Am. Chem. Soc, 2002, 124, 18, 5025-5036.

*Primary Examiner* — John Hardee
(74) *Attorney, Agent, or Firm* — Winston & Strawn LLP

(57) ABSTRACT

The present invention concerns a composition of matter comprising at least 85% w/w of (Z)-4,8-dimethyl-2,7-nonadien-4-ol and at most 15% w/w of (E)-4,8-dimethyl-2,7-nonadien-4-ol, as well as the use as perfuming ingredient of said composition of matter.

16 Claims, No Drawings

SAGE ODORANT

TECHNICAL FIELD

The present invention relates to the field of perfumery. More particularly, it concerns a composition of matter comprising at least 85% w/w of (Z)-4,8-dimethyl-2,7-nonadien-4-ol and at most 15% w/w of (E)-4,8-dimethyl-2,7-nonadien-4-ol. Said composition of matter is a useful perfumery ingredient, and therefore the present invention comprises the invention's compound as part of a perfuming composition or of a perfuming consumer product.

PRIOR ART

To the best of our knowledge, the invention's composition of matter is novel.

However, in the document U.S. Pat. No. 2,838,576 is reported a general formula, encompassing the present composition of matter, which describes compounds useful as perfumery ingredient to confer "bergamot-lavander" odor notes. In said document, there is no mention of specific requirements regarding the double bond configuration, and it is described only an undefined composition of matter of 4,8-dimethyl-2,7-nonadien-4-ol isomers but which has significantly different odor properties (bergamot like) compared to the present composition of matter.

DESCRIPTION OF THE INVENTION

We have now surprisingly discovered that a composition of matter comprising:
at least 85% w/w of (Z)-4,8-dimethyl-2,7-nonadien-4-ol; and
at most 15% w/w of (E)-4,8-dimethyl-2,7-nonadien-4-ol;
the percentage being relative to the total weight of the composition of matter;
can be used as perfuming ingredient, for instance to impart odor notes of the sage type.

Each compound of the present composition of matter can be in the form of any one of its enantiomers or a mixture thereof. According to a particular embodiment, the composition of matter is in a racemic form.

According to a particular embodiment of the invention, the present composition of matter comprises:
at least 90% w/w of (Z)-4,8-dimethyl-2,7-nonadien-4-ol; and
at most 10% w/w of (E)-4,8-dimethyl-2,7-nonadien-4-ol;
the percentage being relative to the total weight of the composition of matter.

According to a particular embodiment of the invention, the present composition of matter consists of essentially (Z)-4,8-dimethyl-2,7-nonadien-4-ol (i.e. the cis isomer accounts for at least 95% w/w). This compound possesses a very natural odor with a clear sage connotation, with floral and spicy/cardamon-coriander aspect. The odor of this compound does not present any, or significant, citrus-bergamot notes. This compound is particularly appreciated by the person skilled in the art for its pronounced clary sage character and its ability to impart/maintain a significant lift and volume to a perfuming composition.

The odor character of the invention's composition of matter is very surprising in to view of the prior art. Indeed, when the odor of the invention's composition of matter is compared with that of the prior art composition of matter (i.e. obtained by the same manner as described in U.S. Pat. No. 2,838,576), or with that of the pure (E)-4,8-dimethyl-2,7-nonadien-4-ol, then the differences are striking, and can be described as in Table 1 herein below.

TABLE 1

4,8-Dimethyl-2,7-nonadien-4-ol isomers and their odor properties

| Compound/composition structure and name | Odor notes |
| --- | --- |
| (Z)-4,8-dimethyl-2,7-nonadien-4-ol | Clear sage connotation, with a floral and spicy/cardamon-coriander aspect. No bergamot notes. |
| (E)-4,8-dimethyl-2,7-nonadien-4-ol | Bergamot, linalyl acetate/linalool, slightly jasmonic. No sage notes |
| Composition containing 65% w/w (Z)-4,8-dimethyl-2,7-nonadien-4-ol and 35% w/w (E)-4,8-dimethyl-2,7-nonadien-4-ol (according to U.S. Pat. No. 2,838,576) | Linalool, bergamot, slightly jasmonic. No sage notes. |
| Composition containing 85% w/w (Z)-4,8-dimethyl-2,7-nonadien-4-ol and 15% w/w (E)-4,8-dimethyl-2,7-nonadien-4-ol | Dominant sage character note. |

Thus the sage character of the (Z) isomer is only perceivable when the (E) is in small amount, otherwise the bergamot character of the (E) dominates the olfactive profile. Said differences lend the invention's composition of matter and the prior art composition of matter to be each suitable for different uses, i.e. to impart different organoleptic impressions.

As mentioned above, the invention concerns the use of the invention's composition of matter as perfuming ingredient. In other words, it concerns a method to confer, enhance, improve or modify the odor properties of a perfuming composition or of a perfumed article, which method comprises adding to said composition or article an effective amount of the invention's composition of matter.

According to a particular embodiment of the invention, said use or method is to impart odor notes of the sage, floral and spicy type.

By "use of the invention's composition of matter" it has to be understood here also the use of any perfuming composition containing the invention's composition of matter and which can be advantageously employed in perfumery industry.

Said perfuming compositions, which in fact can be advantageously employed as perfuming ingredients, are also an object of the present invention.

Therefore, another object of the present invention is a perfuming composition comprising:
i) as perfuming ingredient, the invention's composition of matter as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- und Geliermittel in Lebensmitteln, Band 2 der Schriftenreihe Lebensmittelchemie, Lebensmittelqualität, Behr's Verlag to GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of the invention's composition of matter and at least one perfumery carrier represents a particular embodiment of the invention as to well as a perfuming composition comprising the invention's composition of matter, at least one perfumery carrier, at least one perfumery base, and optionally at least one perfumery adjuvant.

For the sake of clarity, it is also understood that any mixture resulting directly from a chemical synthesis, e.g. a reaction medium without an adequate purification, in which the invention's composition of matter would be involved as a starting, intermediate or end-product could not be considered as a perfuming composition according to the invention as far as said mixture does not provide the inventive composition of matter in a suitable form for perfumery. Thus, unpurified reaction mixtures are generally excluded from the present invention unless otherwise specified.

Furthermore, the invention's composition of matter can also be advantageously used in all the fields of modern perfumery, i.e. fine or functional perfumery, to positively impart or modify the odor of a consumer product into which said invention's composition of matter is added. Consequently, a perfuming consumer product which comprises:
i) as perfuming ingredient, the invention's composition of matter, as defined above; and
ii) a perfumery consumer base;
is also an object of the present invention.

The invention's composition of matter can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of the invention's composition of matter.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's composition of matter, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the composition of matter according to the invention can be incorporated into the various aforementioned articles or compositions vary within a wide range of values. These values are dependent on the nature of the article to be perfumed and on the desired organoleptic effect as well as the nature of the co-ingredients in a given base when the composition of matter according to the invention are mixed with perfuming co-ingredients, solvents or additives commonly used in the art.

For example, in the case of perfuming compositions, typical concentrations are in the order of 0.5% to 40% by weight, or even more, of the invention's composition of matter based on the weight of the composition into which they are incorporated. Concentrations lower than these, such as in the order of 0.01% to 4.0% by weight, can be used when said the invention's composition of matter is incorporated into perfumed articles, percentage being relative to the weight of the article.

The invention's composition of matter, and the (Z)-4,8-dimethyl-2,7-nonadien-4-ol essentially pure, can be prepared according to several methods. As reported in the experimental part, one possibility is the addition of prop-1-yn-1-yl Grignard such as prop-1-yn-1-yl magnesium bromide to 6-methyl-5-hepten-2-one. The triple bond of 4-8-dimethylnon-7-en-2-yn-4-ol obtained is then reduced under appropriate conditions in to order to provide selectively (Z)-4,8-dimethyl-2,7-nonadien-4-ol (e.g. Lindlar catalyst). The same intermediate could also be synthesized by the addition of propyne (or allene) to 6-methyl-5-hepten-2-one under basic conditions as described in DE2228333. Another approach starting from the same starting material as above passes through the acetylene addition providing the 3,7-dimethyloct-6-en-1-yn-3-ol then the methylation of the triple bond and finally, as previously described, the stereoselective hydrogenation of the triple bond (e.g. Lindlar catalyst) leading to (Z)-4,8-dimethyl-2,7-nonadien-4-ol. The addition of acetylene or ethynyl Grignard to 6-methyl-5-hepten-2-one is well documented (as non limited literatures: WO 20075025 or *J. Am. Chem. Soc.* 2002, 124 (18), 5025). A more direct alternative already reported in the literature (U.S. Pat. No. 2,838,576, DE 1005952, *Comptes Rendus Hebdomadaires des Seances de l'Academie des Sciences* 1955, 240, 631) is the addition of the prop-1-en-1-yl Grignard to 6-methyl-5-hepten-2-one.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Preparation of (E)-4,8-dimethyl-2,7-nonadien-4-ol (for Comparative Purpose)

A solution of 4,8-dimethyl-7-nonen-2-yn-4-ol (7.78 g; 44.5 mmol) in dry THF (300 ml) was cooled into an ice-water bath, with stirring under nitrogen. Solid LiAlH$_4$ (2.15 g; 53.8 mmol) was added all at once. After 5 minutes, the cooling bath is removed and the reaction is stirred for one hour, then refluxed for 4 hours. After cooling into an ice-water bath, the reaction was treated cautiously with water (2.2 mml), 5% aq. NaOH (6.6 ml) and water (2.2 ml). The reaction was warmed up to room temperature and stirred until a white slurry was observed. Solid anhydrous sodium sulfate (ca 20 g) was added to the mixture in order to dry the medium. The solid was filtered off, thoroughly rinsed with diethyl ether. The filtrate was concentrated in vacuo. The product was purified by column chromatography on silica gel (eluting with heptanes/ethyl acetate 3:1) followed by bulb-to-bulb distillation (75° C./1.2 mbar). The product was obtained as a liquid (3.8 g; 94% pure by GC; 21.3 mmol; yield: 48%).

$^{13}$C-NMR: 138.08 (d); 131.67 (s); 124.57 (d); 122.61 (d); 72.90 (s); 42.57 (t); 28.01 (q); 25.70 (q); 22.96 (t); 17.70 (q); 17.67 (q).

$^1$H-NMR: 5.67-5.50 (m, 2H); 5.11 (m, 1H); 2.08-1.94 (m, 2H); 1.70 (m, 3H); 1.67 (s, 3H); 1.59 (s, 3H); 1.58-1.50 (m, 2H); 1.25 (s, 3H).

Example 1

Synthesis of the Invention's Composition of Matter

Preparation of a Composition of Matter Comprising at Least 98% of (Z)-4,8-dimethyl-2,7-nonadien-4-ol a) 4,8-dimethyl-7-nonen-2-yn-4-ol A solution of LaCl$_3$.2LiCl (0.6 M in THF, 80 ml; 133 mmol) was added rapidly to neat 6-methyl-5-hepten-2-one (60.6 g; 480 mmol), at room temperature under nitrogen. After 1 hour, the reaction was cooled into an ice-water bath and a solution of isopropenylmagnesium bromide (0.5 M in THF; 800 ml; 400 mmol) was added over a 3 hour period. The reaction was then warmed up to room temperature and stirred for 3 hours. After cooling back to 0° C., a saturated aqueous ammonium chloride solution (500 ml) was added slowly with vigorous stirring. After warming up to room temperature, the reaction was filtered through celite, thoroughly rinsing with diethyl ether. The filtrate was transferred to a sep. funnel and the phases separated. The aqueous phase was re-extracted with diethyl ether. Each organic phase was washed with brine. Combined extracts were dried over sodium sulfate. The product was purified by fractional vacuum distillation through a 20-cm Widmer column. The boiling point of the pure product was 53° C./0.004 mbar. 294 mmol of product were obtained (yield: 74%).

$^{13}$C-NMR: 132.16 (s); 124.09 (d); 83.15 (s); 79.33 (s); 68.43 (s); 43.66 (t); 30.09 (q); 25.71 (q); 23.78 (t); 17.68 (q); 3.45 (q).

$^1$H-NMR: 5.15 (m, 1H); 2.30-2.10 (m, 2H); 2.22 (broad s, 1H); 1.82 (s, 3H); 1.72-1.60 (m, 2H); 1.70 (s, 3H); 1.65 (s, 3H); 1.45 (s, 3H).

b) (Z)-4,8-dimethyl-2,7-nonadien-4-ol

The alcohol obtained from the previous experiment (20 g; 120 mmol) was dissolved in absolute ethanol (100 ml) and hydrogenated at room temperature and normal pressure (ca 1 atm) in presence of Lindlar catalyst (200 mg) until the theoretical amount of hydrogen had been absorbed (2700 ml). The catalyst was filtered off, rinsing with ethanol. The filtrate was concentrated in vacuo. The product was purified by bulb-to-bulb distillation (71° C./1.1 mbar). The product was obtained as a liquid (98% pure by GC; yield: 97%).

$^{13}$C-NMR: 136.66 (d); 131.78 (s); 125.34 (d); 124.55 (d); 74.28 (s); 43.42 (t); 29.08 (q); 25.71 (q); 23.01 (t); 17.64 (q); 14.08 (q).

$^1$H-NMR: 5.52-5.39 (m, 2H); 5.15 (m, 1H); 2.18-1.98 (m, 2H); 1.82 (m, 3H); 1.72 (m, 1H); 1.70 (s, 3H); 1.64-1.58 (m, 2H); 1.62 (s, 3H); 1.36 (s, 3H).

Preparation of Compositions of Matter Comprising (Z)-4,8-dimethyl-2,7-nonadien-4-ol and (E)-4,8-dimethyl-2,7-nonadien-4-ol in Various Ratios Mixtures of desired ratios were obtained by admixing the adequate amount of the above composition comprising at least 98% w/w/ of (Z)-4,8-dimethyl-2,7-nonadien-4-ol described above with the adequate amount of (E)-4,8-dimethyl-2,7-nonadien-4-ol described above.

Example 2

Preparation of a Perfuming Composition

A perfuming composition for shampoos, of the herbaceous-chamomile type, was prepared by admixing the following ingredients:

| Parts by weight | Ingredient |
|---|---|
| 250 | Benzyl acetate |
| 10 | Geranyl acetate |
| 35 | Linalyl acetate |
| 35 | Styrallyl acetate |
| 25 | Aladinate ® [1] |
| 160 | Hexylcinnamic aldehyde |
| 20 | Wormwood essential oil |
| 10 | Methyl benzoate |
| 40 | Ethyl (Z)-2,4-dimethyl-2-pentenoate |
| 35 | Camphor |
| 25 | Carvone Laevo |
| 20 | 10%* Cis-3-Hexenol |
| 10 | Allyl cyclohexylpropionate |
| 400 | Dihydromyrcenol |
| 25 | Estragol |
| 50 | Eucalyptus essential oil |
| 40 | Eugenol |
| 100 | Exaltolide ® [2] |
| 60 | 10%* 2,6,10-Trimethyl-9-undecenal |
| 35 | Fructalate ® [3] |
| 50 | Geraniol |
| 100 | Hedione ® [4] |
| 10 | Allyl heptanoate |
| 10 | Hivernal ® [5] |
| 230 | 2-Phenoxyethyl isobutyrate |
| 15 | Lemonile ® [6] |
| 80 | Lilial ® [7] |
| 50 | Lorysia ® [8] |
| 10 | 10%* Methyl 2-nonynoate |
| 10 | Methylparacresol |
| 30 | Muscenone ™ [9] Delta |
| 240 | Phenethylol |
| 10 | 10%* Pyrazobutyle |
| 80 | Terpineol |
| 50 | 2,4-Dimethyl-3-cyclohexen-1-carboxaldehyde |
| 30 | 10%* Gamma undecalactone |
| 10 | (2,2-Dimethoxyethyl)benzene |
| 2400 | |

*in dipropyleneglycol
[1] 3-methyl-2-hexenyl acetate; origin: Firmenich SA, Geneva, Switzerland
[2] pentadecanolide; origin: Firmenich SA, Geneva, Switzerland
[3] diethyl 1,4-cyclohexane dicarboxylate; origin: Firmenich SA, Geneva, Switzerland
[4] methyl dihydrojasmonate; origin: Firmenich SA, Geneva, Switzerland
[5] 3-(3,3/1,1-dimethyl-5-indanyl)propanal; origin: Firmenich SA, Geneva, Switzerland
[6] 3,7-dimethyl-2/3,6-nonadienenitrile; origin: Givaudan SA, Vernier, Switzerland
[7] 3-(4-tert-butylphenyl)-2-methylpropanal; origin: Givaudan SA, Vernier, Switzerland
[8] 4-(1,1-dimethylethyl)-1-cyclohexyl acetate; origin: Firmenich SA, Geneva, Switzerland
[9] 3-methyl-5-cyclopentadecen-1-one; origin: Firmenich SA, Geneva, Switzerland The addition of 1100 parts by weight of an invention's composition of matter comprising at least 98% of (Z)-4,8-dimethyl-2,7-nonadien-4-ol to the above-described perfuming composition reinforced the herbal connotation (by its sage note) and imparted to the latter a nice balanced cardamom aspect and also brought volume and radiance to the overall fragrance.

When instead of (Z)-4,8-dimethyl-2,7-nonadien-4-ol was added the same amount of the (E)-4,8-dimethyl-2,7-nonadien-4-ol, the new fragrance was flat, too citrus, almost dirty. When instead of the invention's composition was added the same amount of linalool, the new fragrance was much more floral and was missing the herbal complexity of the clary-sage.

Example 3

Preparation of a Perfuming Composition

A perfuming composition for woman, of the floral-musky-woody type, was prepared by admixing the following ingredients:

| Parts by weight | Ingredient |
|---|---|
| 30 | Benzyl acetate |
| 20 | Ambrox ® [1] |
| 440 | Bergamote essential oil |
| 10 | Cashmeran ® [2] |
| 30 | 8-Methoxy-2,6,6,8-tetramethyl-tricyclo[5.3.1.0(1,5)] undecane |
| 30 | 10%* Cis-3-Hexenol |
| 20 | 10%* Damascone Alpha |
| 20 | 10%* Delta Damascone |
| 20 | 10%* Ethylpraline |
| 15 | Ethylvanilline |
| 20 | Exaltenone ® [3] |
| 500 | Exaltolide ® [4] |
| 10 | 2-Methyl-4-(2,2,3-trimethyl-3-cyclopenten-1-yl)-4-penten-1-ol |
| 20 | 3-(4-Methoxyphenyl)-2-methylpropanal |
| 1130 | Hedione ® [5] |
| 30 | Hivernal ® [6] |
| 170 | Ionone Beta |
| 580 | Iso E ® [7] Super |
| 15 | 3-Hexenyl-methyl carbonate |
| 500 | Linalool |
| 55 | Mandarine essential oil |
| 25 | Muscenone ™ [8] Dextro |
| 10 | 10%* Myrrhone ® [9] |
| 85 | 7-Methoxy-3,7-dimethyl-2-octanol |
| 10 | Patchoulol |
| 30 | Pink pepper oil |
| 50 | Orange essential oil |
| 170 | Romandolide ® [10] |
| 25 | Rose oil |
| 200 | Benzyle salicylate |
| 130 | Sclareolate ® [11] |
| 50 | 1-(2,6,10-Trimethyl-1(2),5,9-cyclododecatrien-1-yl)-1-ethanone |
| 10 | 2,4-Dimethyl-3-cyclohexen-1-carboxaldehyde |
| 10 | Gamma undecalactone |
| 25 | 10%* Vanilline |
| 5 | Vulcanolide ® [12] |
| 4500 | |

*in dipropyleneglycol
[1] (−)-(8R)-8,12-epoxy-13,14,15,16-tetranorlabdane; origin: Firmenich SA, Geneva, Switzerland
[2] 1,2,3,5,6,7-hexahydro-1,1,2,3,3-pentamethyl-4-indenone; origin: International Flavors & Fragrances, USA
[3] (Z)-4-cyclopentadecen-1-one
[4] pentadecanolide; origin: Firmenich SA, Geneva, Switzerland
[5] methyl cis-dihydrojasmonate; origin: Firmenich SA, Geneva, Switzerland
[6] 3-(3,3/1,1-dimethyl-5-indanyl)propanal; origin: Firmenich SA, Geneva, Switzerla
[7] 1-(octahydro-2,3,8,8-tetramethyl-2-naphthalenyl)-1-ethanone; origin: Givaudan SA, Vernier, Switzerland
[8] 3-methyl-5-cyclopentadecen-1-one; origin: Firmenich SA, Geneva, Switzerland
[9] 4-(2,2,C-3,t-6-tetramethyl-R-1-cyclohexyl)-3-buten-2-one; origin: Firmenich SA, Geneva, Switzerland
[10] (1S,1'R)-[1-(3',3'-dimethyl-1'-cyclohexyl)ethoxycarbonyl]methyl propanoate; origin: Firmenich SA, Geneva, Switzerland
[11] propyl (S)-2-(1,1-dimethylpropoxy)propanoate; origin: Firmenich SA, Geneva, Switzerland
[12] trans-5,6,7,8-tetrahydro-3,5,5,6,7,8,8-heptamethyl-2-naphthalenecarbaldehyde; origin: Firmenich SA, Geneva, Switzerland The addition of 500 parts by weight of an invention's composition of matter comprising at least 98% of (Z)-4,8-dimethyl-2,7-nonadien-4-ol to the above-described perfuming composition reinforced the floral notes and imparted also a clary sage twist. When instead of the invention's composition was added the same amount of linalool, the new fragrance was much more floral and was missing the clary-sage twist.

What is claimed is:

1. A method to confer, enhance, improve or modify the odor properties of a perfuming composition or of a perfumed article, which method comprises adding to said composition or article an effective amount of a composition of matter comprising:
   at least 85% w/w of (Z)-4,8-dimethyl-2,7-nonadien-4-ol; and
   at most 15% w/w of (E)-4,8-dimethyl-2,7-nonadien-4-ol;
the percentage being relative to the total weight of the composition of matter.

2. The method according to claim 1, wherein said composition of matter comprises:
   at least 90% w/w of (Z)-4,8-dimethyl-2,7-nonadien-4-ol; and
   at most 10% w/w of (E)-4,8-dimethyl-2,7-nonadien-4-ol;
the percentage being relative to the total weight of the composition of matter.

3. The method according to claim 1, wherein said composition consists essentially of (Z)-4,8-dimethyl-2,7-nonadien-4-ol.

4. The method according to claim 1, wherein the conferred odor notes are of the sage, floral and spicy type.

5. A perfuming composition comprising
   i) the composition of matter recited in claim 1;
   ii) at least one ingredient selected from the group consisting of a perfumery carrier and a perfumery base; and
   iii) optionally at least one perfumery adjuvant.

6. A perfuming consumer product comprising:
   i) the composition of matter recited in claim 1; and
   ii) a perfumery consumer base.

7. A perfuming consumer product according to claim 6, wherein the perfumery consumer base is a perfume, a fabric care product, a body-care product, an air care product or a home care product.

8. A perfuming consumer product according to claim 6, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

9. A perfuming composition comprising
   i) the composition of matter as recited in claim 2; and
   ii) at least one ingredient selected from the group consisting of a perfumery carrier and a perfumery base; and
   iii) optionally at least one perfumery adjuvant.

10. A perfuming consumer product according to claim 9, wherein, the perfumery consumer base is a perfume, a fabric care product, a body-care product, an air care product or a home care product.

11. A perfuming consumer product according to claim 9, characterized in that the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

12. A perfuming composition comprising
   i) a composition of matter, as recited in claim 3,
   ii) a least one ingredient selected from the group consisting of a perfumery carrier and a perfumery base; and
   iii) optionally at least one perfumery adjuvant.

13. A perfuming consumer product according to claim 12, wherein the perfumery consumer base is a perfume, a fabric care product, a body-care product, an air care product or a home care product.

14. A perfuming consumer product according to claim 12, characterized in that the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

15. A perfuming consumer product comprising:
   i) the composition of matter recited in claim 2; and
   ii) a perfumery consumer base.

16. A perfuming consumer product comprising:
   i) the composition of matter recited in claim 3; and
   ii) a perfumery consumer base.

* * * * *